(12) United States Patent
Chaparro et al.

(10) Patent No.: US 12,279,990 B2
(45) Date of Patent: Apr. 22, 2025

(54) DEVICES, SYSTEMS, AND METHODS FOR MODULATING TISSUE TEMPERATURE

(71) Applicant: DUKE UNIVERSITY, Durham, NC (US)

(72) Inventors: Rafael Eduardo Chaparro, Durham, NC (US); Paolo Maccarini, Durham, NC (US); Luis Fernando Gonzalez, Durham, NC (US); Donald Pearce, Durham, NC (US); Edward Lysk Wyckoff, III, Durham, NC (US); Syed Faaiz Enam, Durham, NC (US); Jikai Shen, Durham, NC (US); Aliesha O'Raw, Durham, NC (US); Rachel Yang, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 1023 days.

(21) Appl. No.: 17/273,548

(22) PCT Filed: Sep. 6, 2019

(86) PCT No.: PCT/US2019/049988
§ 371 (c)(1),
(2) Date: Mar. 4, 2021

(87) PCT Pub. No.: WO2020/051480
PCT Pub. Date: Mar. 12, 2020

(65) Prior Publication Data
US 2021/0330490 A1    Oct. 28, 2021

Related U.S. Application Data

(60) Provisional application No. 62/727,617, filed on Sep. 6, 2018.

(51) Int. Cl.
*A61F 7/12* (2006.01)
*A61F 7/00* (2006.01)

(52) U.S. Cl.
CPC ............... *A61F 7/12* (2013.01); *A61F 7/007* (2013.01); *A61F 2007/0002* (2013.01);
(Continued)

(58) Field of Classification Search
CPC ........................... A61F 7/12; A61F 2007/126
See application file for complete search history.

(56) References Cited

U.S. PATENT DOCUMENTS

| 6,436,131 B1 | 8/2002 | Ginsburg |
| 6,726,653 B2 | 4/2004 | Noda et al. |

(Continued)

FOREIGN PATENT DOCUMENTS

WO    WO 2002/089685    11/2002

OTHER PUBLICATIONS

International Search Report and Written Opinion for PCT/US19/49988. Mailed Nov. 20, 2019. 15 pages.

*Primary Examiner* — Kaitlyn E Smith
(74) *Attorney, Agent, or Firm* — Casimir Jones, S.C.; Peter J. Schlueter

(57) ABSTRACT

This present disclosure provides devices, systems, and methods relating to the modulation of tissue temperature. In particular, the present disclosure provides devices, systems, and methods for rapidly cooling or heating tissue in a subject as a therapeutic and/or prophylactic means for treating tissue that has been injured or damaged.

32 Claims, 5 Drawing Sheets
(4 of 5 Drawing Sheet(s) Filed in Color)

(52) U.S. Cl.
CPC .............. *A61F 2007/0056* (2013.01); *A61F 2007/0076* (2013.01); *A61F 2007/126* (2013.01)

(56) References Cited

U.S. PATENT DOCUMENTS

| | | | |
|---|---|---|---|
| 7,156,867 B2* | 1/2007 | Lennox | A61F 7/02 |
| | | | 607/113 |
| 8,202,308 B2* | 6/2012 | Smyth | A61F 7/12 |
| | | | 607/113 |
| 2004/0181269 A1 | 9/2004 | Lee | |
| 2008/0168775 A1 | 7/2008 | Windheim et al. | |
| 2014/0214140 A1* | 7/2014 | Ginsburg | H10K 50/828 |
| | | | 607/113 |

* cited by examiner

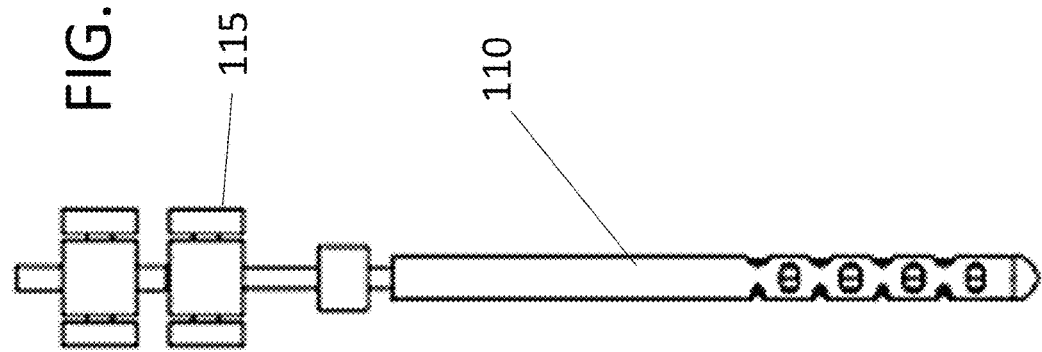
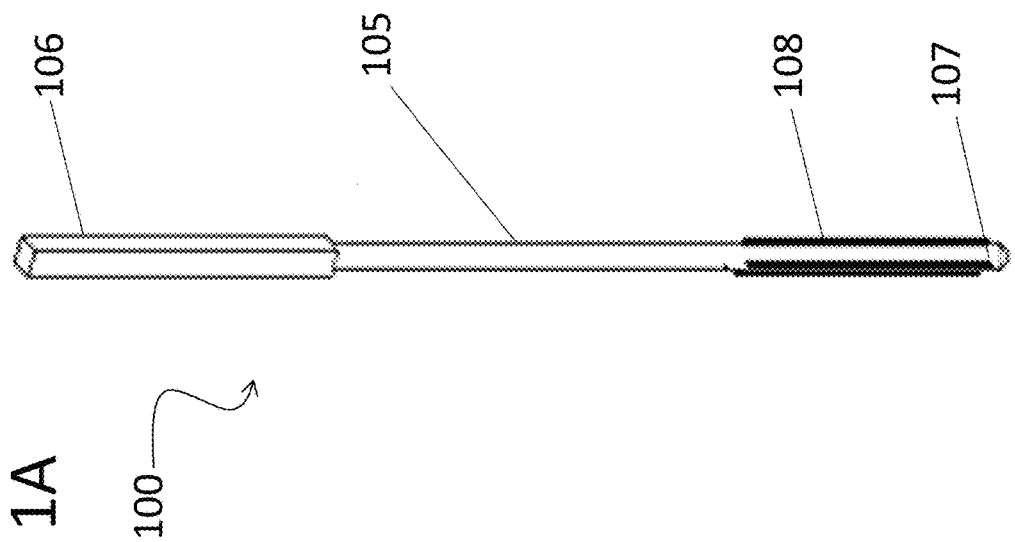
FIG. 1A
FIG. 1B
FIGS. 1A-1B

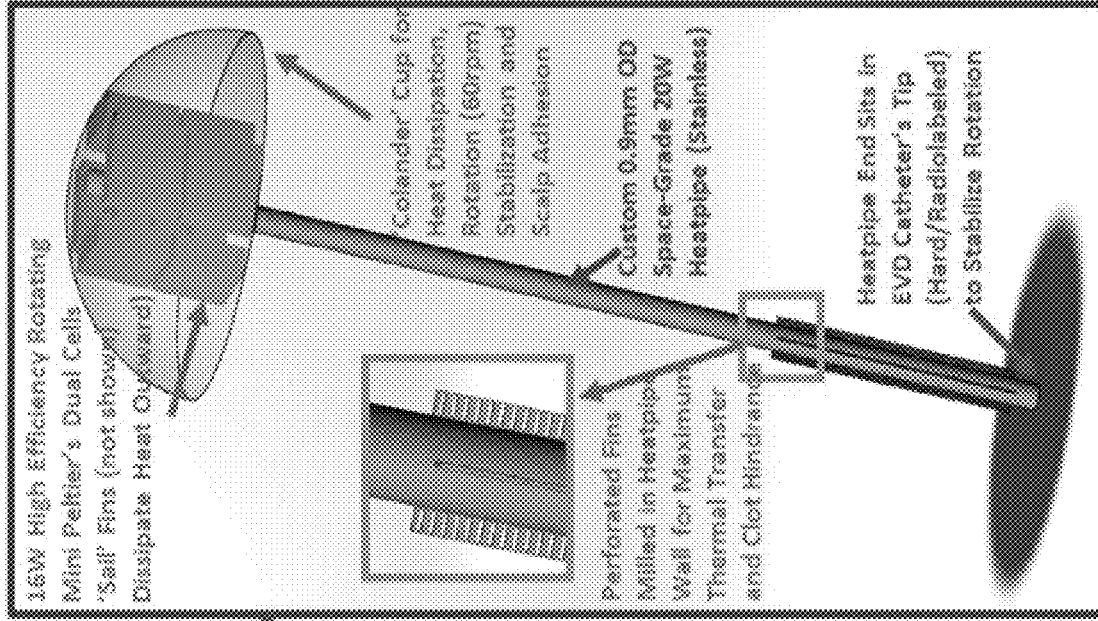
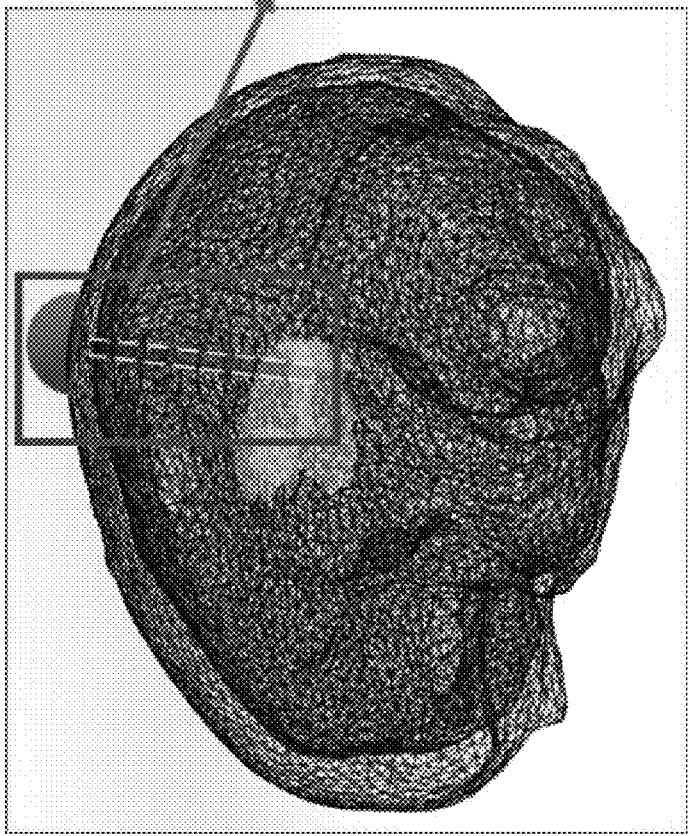
FIG. 3A
FIG. 3B
FIGS. 3A-3B

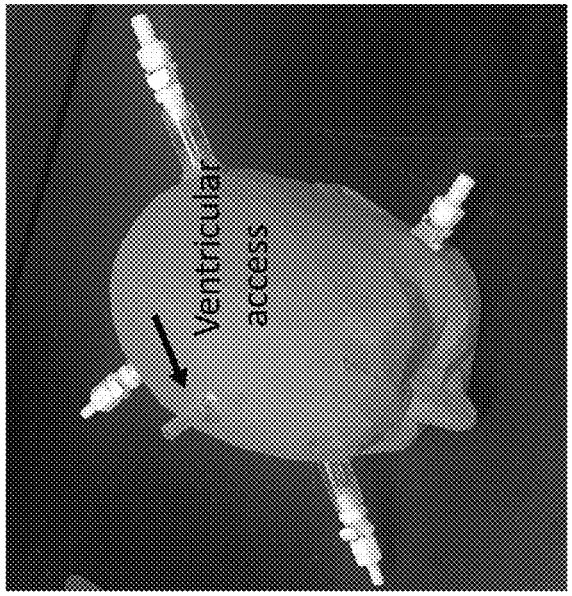
FIG. 5A
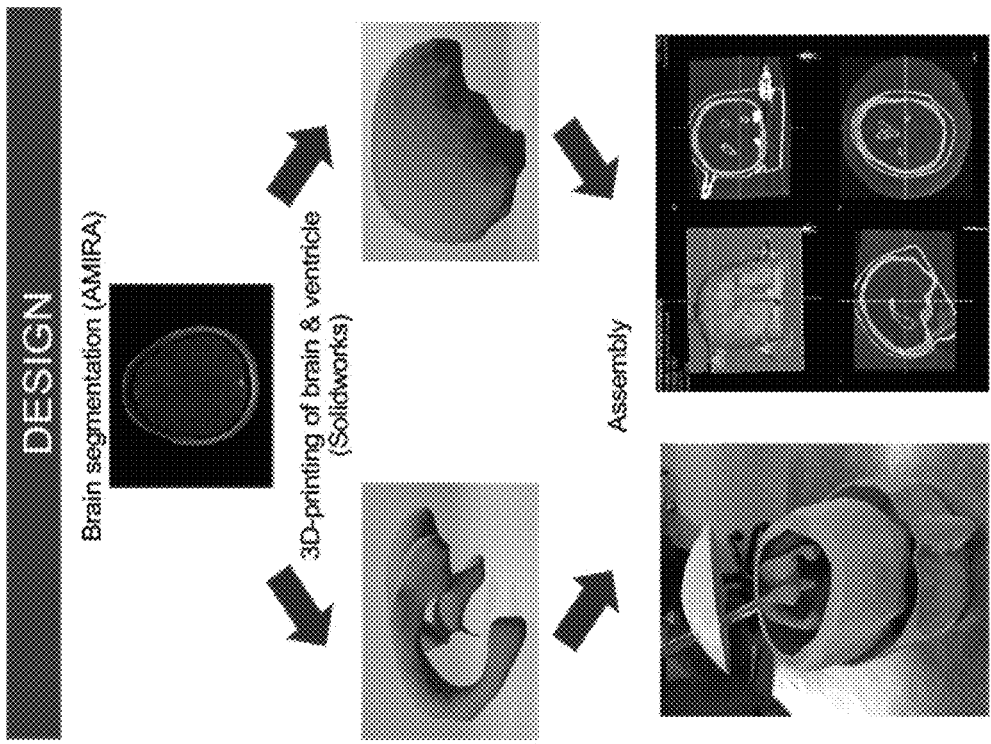
FIG. 5B
FIGS. 5A-5B

DEVICES, SYSTEMS, AND METHODS FOR MODULATING TISSUE TEMPERATURE

RELATED APPLICATIONS

This application is a national phase application under 35 U.S.C. § 371 of PCT International Application No. PCT/US2019/049988, filed Sep. 6, 2019, which claims priority to and the benefit of U.S. Provisional Patent Application No. 62/727,617 filed Sep. 6, 2018, each of which is incorporated herein by reference in their entirety for all purposes.

FIELD

This present disclosure provides devices, systems, and methods relating to the modulation of tissue temperature. In particular, the present disclosure provides devices, systems, and methods for rapidly cooling or heating tissue in a subject as a therapeutic and/or prophylactic means for treating tissue that has been injured or damaged.

BACKGROUND

Millions of people worldwide suffer annually from traumatic brain injuries, stroke, status epilepticus and global ischemia (heart attack), and other traumatic bodily injuries. These insults often result is significant tissue damage and even tissue loss unless rapidly and properly treated. In some cases, such as in the brain, damage or injury can lead to mortality and long-term neurological morbidity unless rapidly and properly treated. One effective means for reducing significant damage following an injury is hypothermia. By rapidly cooling damaged tissue, for example, it is possible to dramatically reduce inflammation, metabolism, and oxygen consumption, ultimately preserving tissue function. In other cases, rapidly heating tissue (hyperthermia) can be used to address a variety of conditions such as brain tumors, cavernous malformations, brain metastasis, headaches, migraines, and joint stiffness, and it can be used for various rehabilitative purposes. The therapeutic effects of heat can include increasing the extensibility of collagen tissues, decreasing joint stiffness, reducing pain, relieving muscle spasms, reducing inflammation, and reducing edema; heat therapy can also be used in the post-acute phase of healing to increase blood flow. Thus, there is a need for a device that can rapidly cool or heat damaged tissue in a subject.

SUMMARY

Embodiments of the present disclosure include a device for modulating the temperature, without fluid or gas exchange, of a tissue in a subject. In accordance with these embodiments, the device includes a heat exchanger comprising a proximal end and a distal end, the distal end comprising a plurality of fins, at least one thermoelectric modulator coupled to the proximal end of the heat exchanger, and a motor functionally coupled to the at least one thermoelectric modulator, wherein the at least one thermoelectric modulator and the motor are detachably connected to the heat exchanger.

In some embodiments, the heat exchanger includes a heat pipe. In some embodiments, the heat pipe comprises a sealed vacuum tube. In some embodiments, the heat pipe is sized and configured for insertion into a catheter.

In some embodiments, the plurality of fins extends longitudinally along a portion of the distal end of the heat exchanger. In some embodiments, the plurality of fins are perforated. In some embodiments, the heat exchanger is rotatable around its longitudinal axis. In some embodiments, the plurality of fins are rotatable around the longitudinal axis of the heat exchanger. In some embodiments, the plurality of fins are arranged in one or more linear rows extending longitudinally along a portion of the distal end of the heat exchanger. In some embodiments, the plurality of fins are arranged in one or more spirals along a portion of the distal end of the heat exchanger.

In some embodiments, the at least one thermoelectric modulator includes one or more Peltier cells. In some embodiments, the at least one thermoelectric modulator includes from 2 to 20 Peltier cells. In some embodiments, the one or more Peltier cells are functionally coupled to each other. In some embodiments, the motor supplies power to the one or more Peltier cells and/or the rotatable heat exchanger. In some embodiments, the application of power to the heat exchanger causes the heat exchanger to rotate around its longitudinal axis. In some embodiments, the application of power to the one or more Peltier cells causes the one or more Peltier cells to oscillate continuously in a back-and-forth manner, thereby modulating the temperature of the tissue. In some embodiments, the application of power to the one or more Peltier cells modulates the temperature in the tissue of the subject at a rate of at least $\pm 0.5°$ C./min.

In some embodiments, modulating the temperature of the tissue in the subject includes reducing the temperature of the tissue. In some embodiments, modulating the temperature of the tissue in the subject includes increasing the temperature of the tissue.

In some embodiments, the devices described above further include one or more heat dissipation elements located at the proximal end of the device. In some embodiments, one or more heat dissipation elements includes at least one of a plurality of fins, a motorized fan, and/or a coolant fluid.

In some embodiments, the at least one thermoelectric modulator and the motor are contained within a housing. In some embodiments, the housing is concave and semi-circular. In some embodiments, the housing further contains one or more heat dissipation elements.

Embodiments of the present disclosure also include a system for modulating the temperature of a tissue in a subject. In accordance with these embodiments, the system includes any embodiments of the device described above, a catheter, and a power source for operating the device.

Embodiments of the present disclosure also include a method for modulating the temperature of a tissue of a subject. In accordance with these embodiments, the method includes inserting any embodiments of the device described above into a catheter, wherein the catheter is positioned within or adjacent to the tissue, and applying power to the device, thereby modulating the temperature of the tissue.

In some embodiments, the device is inserted into a fluid filled cavity adjacent to the tissue. In some embodiments, the tissue is solid organ tissue, and wherein the device is inserted directly into the solid organ tissue. In some embodiments, the tissue has been injured or damaged. In some embodiments, the tissue is brain tissue. In some embodiments, the catheter is perforated.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIGS. 1A-1B include representative diagrams of tissue temperature modulation devices with (FIG. 1B) and without (FIG. 1A) a thermoelectric modulator coupled to the proximal end of the heat exchanger, according to one embodiment of the present disclosure.

FIGS. 3A-3B include representative schematics of the placement of a tissue temperature modulation device into the brain ventricle of a subject (FIG. 3A), and a diagram of the device that includes a plurality of fins at the distal end and heat dissipation elements located at the proximal end of the device, according to one embodiment of the present disclosure.

FIGS. 5A-5B include representative design diagrams for a multi-physic numerical model generated using Comsol/Ansys with variable anatomical and physiological parameters (e.g., thermal/fluid/mechanical properties, perfusion and metabolic rates), which can be used to find the optimized geometry and material for testing the devices and systems of the present disclosure. FIG. 5B shows a 3D-printed phantom with probe inserts to measure temperature and the ventricular catheter access port.

DETAILED DESCRIPTION

Figure 2A:
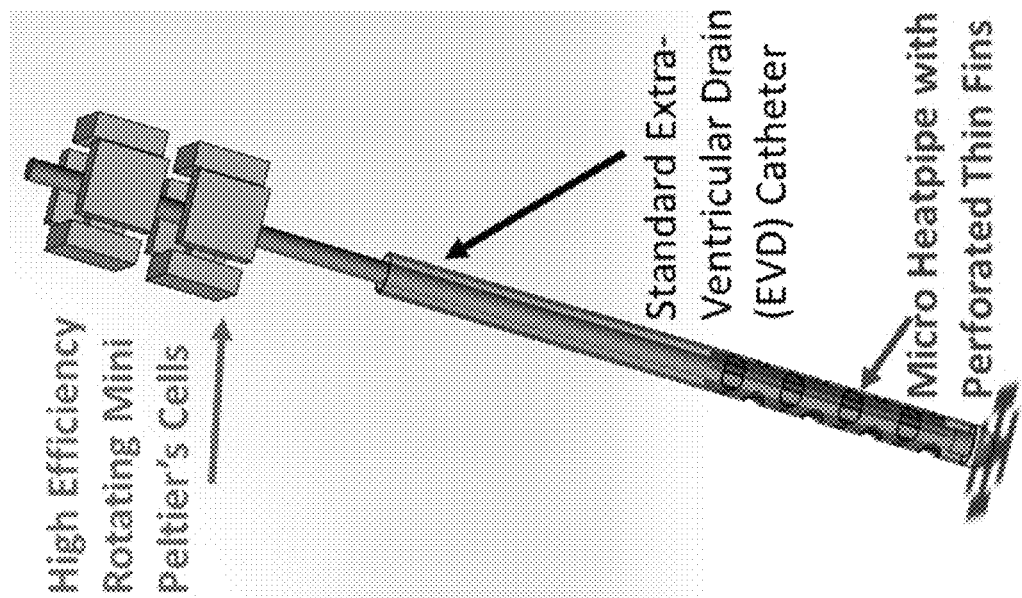
FIGS. 2A-2B include representative perspective views of tissue temperature modulation devices, with the distal ends inserted into a catheter, according to one embodiment of the present disclosure.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

"Therapy" and/or "therapy regimen" generally refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. In some embodiments, the treatment comprises the treatment, alleviation, and/or lessening of pain.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, neurobiology, microbiology, genetics, electrical stimulation, neural stimulation, neural modulation, and neural prosthesis described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Tissue Temperature Modulation Devices

Every year millions of people suffer a major brain insult, including severe traumatic brain injuries, stroke, uncontrolled epilepsy or global ischemia following cardiac arrest.

For instance, stroke is the fifth most common cause of death, and the number one cause of disability. For the 90% of strokes that are ischemic, there are few effective treatments, which include intravenous tissue plasminogen activator (IV-tPA) and mechanical thrombectomy, where blood flow is reestablished by reopening the occluded artery. The latter approach has been validated in multiple randomized clinical studies, but outcomes depend on intervention timing. Similarly, intervention delays and limited therapeutic options plague the treatment of hemorrhagic strokes, global ischemia and traumatic brain injuries.

Conversely, rapid cooling of the brain has shown significant promise in limiting the brain damage to the neural tissue that has irreversibly progressed to infarction. By rapidly shutting down inflammatory responses, oxygen consumption and overall brain metabolism, hypothermia minimizes the extent of secondary injury as an acute or subacute treatment strategy. Inducing control hypothermia has shown beneficial effects in multiple animal models (ischemia, traumatic brain injury-TBI, intracranial hypertension-IH and even status epilepticus). When achieved properly, even mild therapeutic hypothermia (34° C.-35.9° C.) has shown a notable positive impact on neurological outcome in humans following acute brain injuries. In the particular case of TBI and IH patients, there is a remarkable increase in favorable neurological outcome when brain cooling is performed. Despite these results, however, current therapeutic hypothermia is only accepted as standard of treatment for global ischemia after cardiac arrest. For other brain injuries, the positive preclinical results of therapeutic hypothermia are not easily translated into clinical practice, mainly because of the inability to cool efficiently, conveniently, and safely the human brain. Currently available external pads/caps or intravascular saline circulating systems only cool the brain indirectly, and are not therapeutically effective. Additionally, current techniques that selectively decrease cerebral temperature (not systemically) rely on multi-lumen (or balloon) intraventricular catheters that require fluid or gas circulation through pumps. However, since these systems require a fluid exchanges or volume increase, potentially elevating the intracranial pressure and the risk of infection, these technologies have not been widely adopted or commercialized.

Embodiments of the present disclosure include devices, systems, and methods relating to the modulation of tissue temperature without fluid or gas exchange. In particular, the present disclosure provides devices, systems, and methods for directly and rapidly cooling or heating tissue in a subject as a therapeutic and/or prophylactic means for treating tissue that has been injured or damaged.

In accordance with these embodiments, and as shown in FIGS. 1A-1B, the device (100) includes a heat exchanger (105) comprising a proximal end (106) and a distal end (107). The heat exchanger is generally used as a conduit for the rapid exchange of heat from one end of the device to the other. This includes facilitating the removal of heat from (e.g., cooling) and the generation of heat to (e.g., heating) a target tissue in a subject. In some embodiments, the heat exchanger (105) is cylindrically shaped and resembles a pipe (e.g., heat pipe). In some embodiments, the heat exchanger (105) is configured for insertion into a catheter, such as an external ventricular drain (EVD) catheter (FIG. 1B; 110), which facilitates the exchange of heat from the brain ventricle of a subject. In some embodiments, the heat exchanger (105) is rotatable around its longitudinal axis. In some embodiments, the heat exchanger (105) comprises a rotatable heat pipe that is vacuum sealed. In some embodiments, the heat pipe includes a small amount of liquid vapor to aid in the rapid transfer or heat to or from the target tissue in a subject.

In some embodiments, the heat modulation devices of the present disclosure include a plurality of fins (108) at the distal end (107) of the heat exchanger (105). The plurality of fins can be sized and configured for various uses. For example, the plurality of fins (108) can be configured to extend laterally from the longitudinal axis of the heat exchanger (105) to increase the surface area available for transferring heat to or from the target tissue in order to improve heat exchange. In some embodiments, the plurality of fins (108) are extensions of the heat exchanger (105) and do not include slots or perforations. In some embodiments, the plurality of fins (108) are separate components from the heat exchanger (105) and are functionally coupled to the heat exchanger (105). In other embodiments, the plurality of fins (108) can be perforated or slotted.

In some embodiments, the plurality of fins (108) are rotatable within the catheter, which helps to break apart the debris and also helps circulate the bodily fluid to aid in the heat transfer. In accordance with these embodiments, the catheter can include a plurality of perforations or slots to break apart debris or occlusions present in bodily fluid (e.g., CSF) to prevent the debris or occlusions from entering the catheter or circulating through the subject. In some embodiments, the plurality of fins (108) can be rotatable around the longitudinal axis of the heat exchanger (see, e.g., FIG. 3B).

In some embodiments, the plurality of fins (108) extend longitudinally along a portion of the distal end (107) of the heat exchanger (FIG. 1A; 105). In some embodiments, the plurality of fins (108) are arranged in one or more linear rows extending longitudinally along a portion of the distal end of the heat exchanger (FIG. 1A; 105). In some embodiments, the plurality of fins are arranged in one or more spirals along a portion of the distal end (107) of the heat exchanger (105). As would be recognized by one of ordinary skill in the art based on the present disclosure, the plurality of fins (108) can be configured in many other ways to augment the transfer of heat to or from a target tissue.

The heat modulation devices of the present disclosure can also include at least one thermoelectric modulator (115) coupled to the proximal end (106) of the heat exchanger (FIG. 1B). The thermoelectric modulator (115) is generally used as a means for establishing a temperature differences between the device and the target tissue that facilitates the transfer of heat to and from the target tissue. In some embodiments, the thermoelectric modulator (115) is detachably coupled to the proximal end (106) of the heat exchanger (105) (FIG. 1B). The thermoelectric modulator (115) can also be functionally coupled to a motor, which can also be detachably coupled to the proximal end (106) of the heat exchanger (105) (FIG. 1B).

In some embodiments, the at least one thermoelectric modulator (115) includes one or more Peltier cells or modules. As would be recognized by one of ordinary skill in the art based on the present disclosure, Peltier cells are electronic devices designed for maintaining objects at a specific temperature by controlled heating or cooling. Peltier cells can be used to address thermal issues and cool or heat objects where conventional heating/cooling means are not sufficient. Additionally, Peltier cells and an appropriate control circuit/motor can provide the ability to maintain an object (e.g., target tissue) at a specific temperature even under rapidly fluctuating thermal loads. In some embodiments, the at least one thermoelectric modulator (115) includes one or more Peltier cells to transfer heat to or from a target tissue. In some embodiments, the at least one thermoelectric modulator includes from 2 to 20 Peltier cells, from 2 to 18 Peltier cells, from 2 to 16 Peltier cells, from 2 to 14 Peltier cells, from 2 to 12 Peltier cells, from 2 to 10 Peltier cells, from 2 to 8 Peltier cells, from 2 to 6 Peltier cells, or from 2 to 4 Peltier cells (see, e.g., FIGS. 2A-2B).

In some embodiments, the one or more Peltier cells are functionally coupled to each other. In some embodiments, the motor supplies power to one or more Peltier cells in a manner that either generates heat to be transferred to the heat exchanger (105) and then to a target tissue, or to establish a heat sink, in which heat is transferred from the target tissue to the heat exchanger (105) and then released from the proximal end of the device (106). In some embodiments, the motor supplies power to the heat exchanger (105) and causes it to rotate along its longitudinal axis.

Figure 2B:
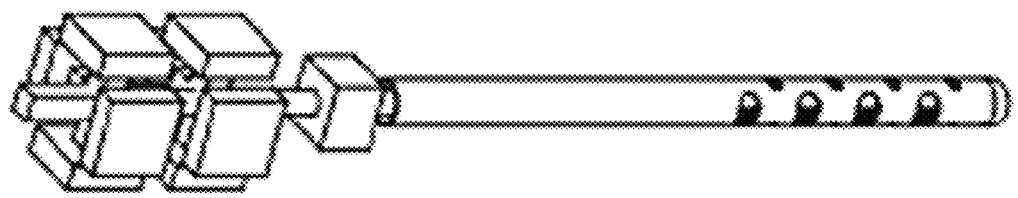

In some embodiments, the application of power to the Peltier cells causes the Peltier cells to oscillate continuously in a back-and-forth manner, thereby modulating the temperature of the tissue (FIGS. 2A-2B). In some embodiments, the application of power to one or more Peltier cells causes the Peltier cells to rotate continuously around the longitudinal axis of the device, thereby modulating the temperature of the tissue. In some embodiments, the application of power to the Peltier cells modulates the temperature in the tissue of the subject at a rate of at least ±0.5° C./min, at least ±0.6° C./min, at least ±0.7° C./min, at least ±0.8° C./min, at least ±0.9° C./min, at least ±1.0° C./min, at least ±1.5° C./min, or at least ±2.0° C./min. In accordance with these embodiments, the heat modulation devices and systems of the present disclosure can be used to modulate the temperature of a tissue in a subject, such that modulation includes reducing the temperature of the tissue or increasing the temperature of the tissue, as compared to the systemic temperature of the surrounding tissue or the systemic temperature of the subject.

The heat modulation devices of the present disclosure can also include one or more heat dissipation elements (e.g., heat sink) located at the proximal end of the device (FIGS. 3A-3B). In some embodiments, the heat dissipation elements can include a plurality of fins, a motorized fan, and/or a coolant fluid. For example, a plurality of heat dissipation fins can extend outwardly and/or radially from the proximal end (106) of the heat exchanger (105), near the thermoelectric modulator (115), to increase the surface area available for heat transfer. In other embodiments, the heat dissipation elements can include a motorized fan to remove heat from the proximal end (106) of the heat exchanger (105), or a coolant fluid contained in a tube. Other such heat dissipation elements can also be used, as would be recognized by one of ordinary skill in the art based on the present disclosure.

In some embodiments, the thermoelectric modulator (115) and the motor are contained within a housing (FIGS. 3A-3B). In some embodiments, the housing is concave and semi-circular in shape. In some embodiments, the housing further contains one or more heat dissipation elements contained within it, which facilitate the rapid transfer of heat from or to a target tissue.

Figure 4:
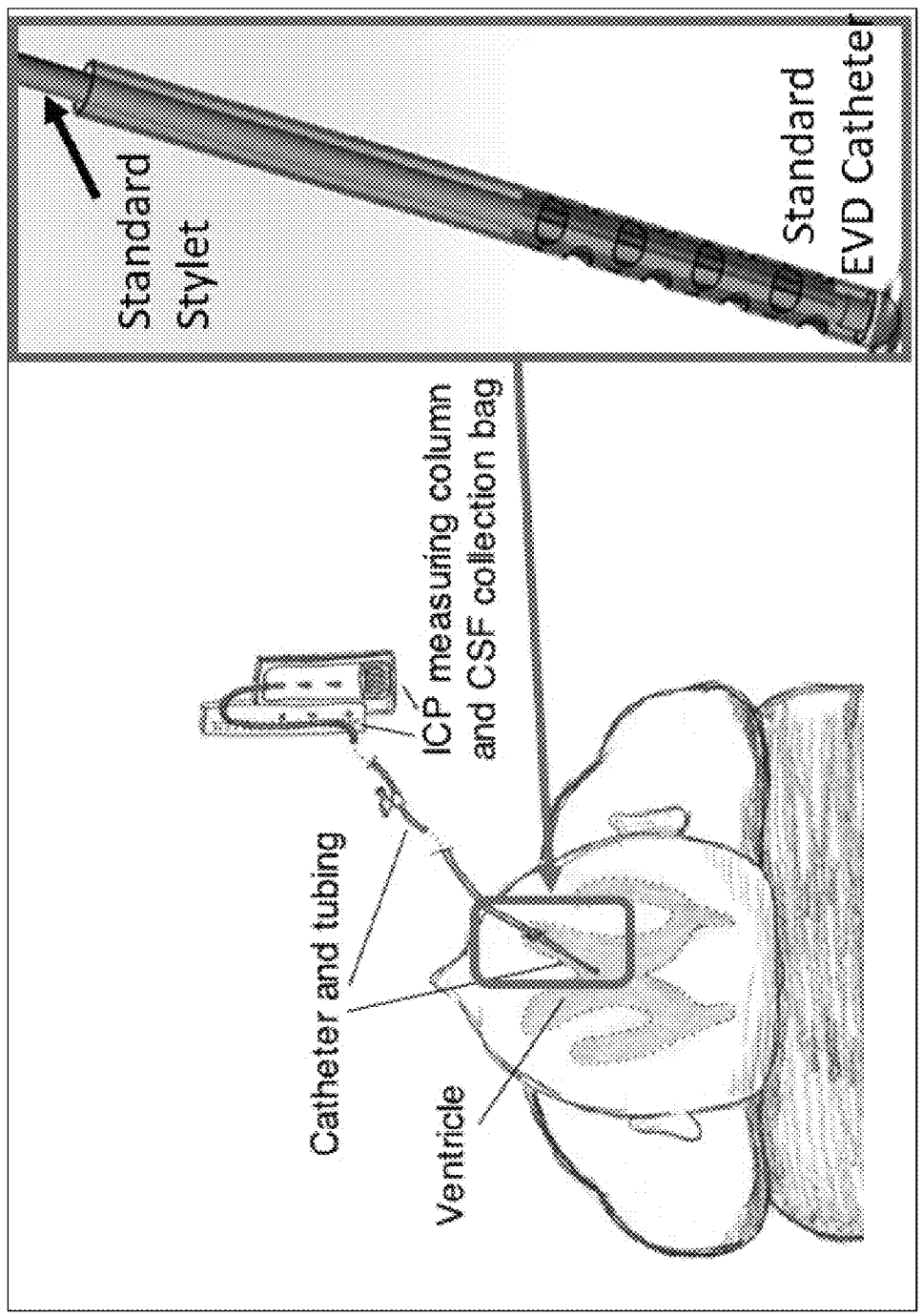
FIG. 4 includes a representative diagram of the placement of the temperature modulation device into a catheter (e.g., external ventricular drain catheter, or EVD catheter) that has been inserted into a brain ventricle of a subject; the system also includes an ICP measuring column and a CSF collection bag, according to one embodiment of the present disclosure.

In a particular embodiment of the present disclosure, the heat modulation device includes a heat pipe as the heat exchanger and four perforated blades (e.g., fins) milled from the 0.5 mm thick heat pipe wall at the distal end of the heat pipe (FIGS. 3A-3B). In other embodiments, the heat modulation device includes a heat pipe as the heat exchanger and blades (e.g., fins) that are not perforated. In other embodiments, the blades (e.g., fins) are coupled to the heat pipe as a separate component of the device. Additionally, eight 2-stage Peltier micromodules can be embedded into a removable collar that is coupled to the heat pipe and have brush contacts to positive and negative supply rings to allow rotation. The heat pipe is held axially between the motor's hollow shaft and the concave hard (and optionally radiolabeled) tip of the EVD catheter. The Peltier micromodules can include multiple heat-dissipating sail-shaped fins that act as a heatsink and are contained in a colander-like cup, where the motor head is mounted and medical adhesive provides the bond to the scalp (FIG. 4). The power for operating the Peltier cells and motor can be supplied via USB-linked box, for example. Labview and Matlab can be used to provide algorithms and a user interface.

3. Methods and Systems

Embodiments of the present disclosure also include a system for modulating the temperature of a tissue in a subject without fluid or gas exchange. In accordance with these embodiments, the system includes the heat modulation devices described herein, as well as a catheter, and a power source for operating the device (FIG. 4). As would be recognized by one of ordinary skill in the art based on the present disclosure, the systems can include other components that aid in the treatment of a patient by removing heat from or generating heat in a target tissue. For example, the systems can include an ICP measuring column, a CSF collection bag, a thermometer at the tip to measure target temperature, and means for imaging the target tissue and/or device as it is placed in a target tissue.

In accordance with these embodiments, the present disclosure also provides methods for modulating the temperature of a tissue of a subject. In some embodiments, the method includes inserting a temperature modulation device described herein into a catheter. In some embodiments, the catheter is positioned within or adjacent to the target tissue prior to insertion of the device. In some embodiments, the method includes applying power to the device to create heat that is transferred to the distal end of the device placed in the subject, or to create a heat sink at the proximal end of the device to transfer heat from the tissue (FIG. 4).

In some embodiments, the device is inserted into a fluid filled cavity adjacent to the target tissue. In some embodiments, the tissue is solid organ tissue (e.g., liver, brain kidney, etc.), and the device is inserted directly into the solid organ tissue (with or without a catheter). In some embodiments, the tissue has been injured or damaged and heating or cooling the tissue treats the injury or lessens the severity of the damage. In some embodiments, the tissue is brain tissue. In some embodiments, the distal end of the device is inserted into a fluid-filled cavity and heating or cooling the fluid in the cavity treats the injury or lessens the severity of the damage.

As shown in FIGS. 5A-5B, and based on segmenting MRI images of a stroke patient, a multi-physic numerical model was generated (using Comsol/Ansys) with variable anatomical and physiological parameters (e.g., thermal/fluid/mechanical properties, perfusion and metabolic rates). This model was used to find the optimized geometry and material for testing the devices and systems of the present disclosure. It was estimated that about 13W could be removed the brain to achieve −0.5° C./min cooling.

Additionally, by using four circulating ports that run fluid through open-cell foam in a 3D printed skull/ventricle assembly (FIG. 5B), fluid dynamics in the brain can be modeled. FIG. 5B shows a 3D-printed phantom with probe inserts to measure temperature and the ventricular catheter access port. According to the model, using eight micro-Peltier cells in series can produce a net heat transfer capability of about 16W. Assuming the ventricle has a volume of 25 mL and cerebrospinal fluid has a heat capacity of 4096 J/kg*° C., the entire volume of fluid in the ventricle will require approximately 102 J/° C. to cool. This will enable the induction of clinically relevant hypothermic temperatures of 32-33° C. within 30-35 minutes.

What is claimed is:

1. A device for modulating temperature of a tissue in a subject, the device comprising:
    a heat exchanger comprising a proximal end and a distal end, wherein the distal end of the heat exchanger comprises a plurality of perforated fins; and
    at least one thermoelectric modulator coupled to the proximal end of the heat exchanger.

2. The device of claim 1, wherein the heat exchanger comprises a heat pipe.

3. The device of claim 2, wherein the heat pipe is sized and configured for insertion into a catheter.

4. The device of claim 1, wherein the heat exchanger is rotatable around its longitudinal axis.

5. The device of claim 1, wherein the plurality of fins extend longitudinally along a portion of the distal end of the heat exchanger.

6. The device of claim 1, wherein the plurality of fins are rotatable around the longitudinal axis of the heat exchanger.

7. The device of claim 1, wherein the at least one thermoelectric modulator comprises from 2 to 20 Peltier cells, and wherein the Peltier cells are functionally coupled.

8. The device of claim 1, wherein the device further comprises a motor functionally coupled to the at least one thermoelectric modulator.

9. The device of claim 8, wherein the at least one thermoelectric modulator and the motor are detachably connected to the heat exchanger.

10. The device of claim 8, wherein the motor supplies power to the heat exchanger and causes the heat exchanger to rotate around its longitudinal axis.

11. The device of claim 8, wherein the motor supplies power to one or more Peltier cells and causes the one or more Peltier cells to rotate continuously in a back-and-forth manner with respect to the longitudinal axis of the heat exchanger.

12. The device of claim 11, wherein supplying the power to the one or more Peltier cells modulates the temperature in the tissue of the subject at a rate of at least ±0.5° C./min.

13. The device of claim 12, wherein modulating the temperature of the tissue in the subject comprises reducing the temperature of the tissue.

14. The device of claim 12, wherein modulating the temperature of the tissue in the subject comprises increasing the temperature of the tissue.

15. The device of claim 1, wherein the device further comprises one or more heat dissipation elements located at the proximal end of the device.

16. The device of claim 15, wherein the one or more heat dissipation elements comprises at least one of a plurality of fins, a motorized fan, and/or a coolant fluid.

17. A method for modulating the temperature of brain tissue of a subject, the method comprising inserting the device of claim 1 into a catheter, wherein the catheter is positioned within a fluid filled cavity adjacent to the brain tissue, and applying power to the device, thereby modulating the temperature of the brain tissue.

18. A device for modulating temperature of a tissue in a subject, the device comprising:
    a heat exchanger comprising a proximal end and a distal end;
    at least one thermoelectric modulator coupled to the proximal end of the heat exchanger; and
    a motor functionally coupled to the at least one thermoelectric modulator, wherein the motor supplies power to the heat exchanger and causes the heat exchanger to rotate around its longitudinal axis.

19. The device of claim 18, wherein the heat exchanger comprises a heat pipe.

20. The device of claim 19, wherein the heat pipe is sized and configured for insertion into a catheter.

21. The device of claim 18, wherein the motor supplies power to one or more Peltier cells and causes the one or more Peltier cells to rotate continuously in a back-and-forth manner with respect to the longitudinal axis of the heat exchanger.

22. The device of claim 21, wherein supplying the power to the one or more Peltier cells modulates the temperature in the tissue of the subject at a rate of at least ±0.5° C./min.

23. The device of claim 18, wherein the device further comprises one or more heat dissipation elements located at the proximal end of the device.

24. The device of claim 23, wherein the one or more heat dissipation elements comprises at least one of a plurality of fins, a motorized fan, and/or a coolant fluid.

25. A method for modulating the temperature of brain tissue of a subject, the method comprising inserting the device of claim 18 into a catheter, wherein the catheter is positioned within a fluid filled cavity adjacent to the brain tissue, and applying power to the device, thereby modulating the temperature of the brain tissue.

26. The device of claim 23, wherein the one or more heat dissipation elements comprises at least one of a plurality of fins, a motorized fan, and/or a coolant fluid.

27. A device for modulating temperature of a tissue in a subject, the device comprising:
    a heat exchanger comprising a proximal end and a distal end;
    at least one thermoelectric modulator coupled to the proximal end of the heat exchanger; and
    a motor functionally coupled to the at least one thermoelectric modulator wherein the motor supplies power to one or more Peltier cells and causes the one or more Peltier cells to rotate continuously in a back-and-forth manner with respect to the longitudinal axis of the heat exchanger,
    wherein the heat exchanger comprises a heat pipe.

28. The device of claim 27, wherein the heat pipe is sized and configured for insertion into a catheter.

29. A device for modulating temperature of a tissue in a subject, the device comprising:
    a heat exchanger comprising a proximal end and a distal end;
    at least one thermoelectric modulator coupled to the proximal end of the heat exchanger; and
    a motor functionally coupled to the at least one thermoelectric modulator wherein the motor supplies power to one or more Peltier cells and causes the one or more Peltier cells to rotate continuously in a back-and-forth manner with respect to the longitudinal axis of the heat exchanger, wherein the motor supplies power to the heat exchanger and causes the heat exchanger to rotate around its longitudinal axis.

30. A device for modulating temperature of a tissue in a subject, the device comprising:
    a heat exchanger comprising a proximal end and a distal end;

at least one thermoelectric modulator coupled to the proximal end of the heat exchanger; and a motor functionally coupled to the at least one thermoelectric modulator, wherein the motor supplies power to one or more Peltier cells and causes the one or more Peltier cells to rotate continuously in a back-and-forth manner with respect to the longitudinal axis of the heat exchanger, wherein the device further comprises one or more heat dissipation elements located at the proximal end of the device.

31. The device of claim 30, wherein the one or more heat dissipation elements comprises at least one of a plurality of fins, a motorized fan, and/or a coolant fluid.

32. A method for modulating the temperature of a tissue of a subject, the method comprising inserting a device for modulating temperature of a tissue in a subject, the device comprising:

a heat exchanger comprising a proximal end and a distal end;

at least one thermoelectric modulator coupled to the proximal end of the heat exchanger; and a motor functionally coupled to the at least one thermoelectric modulator, wherein the motor supplies power to one or more Peltier cells and causes the one or more Peltier cells to rotate continuously in a back-and-forth manner with respect to the longitudinal axis of the heat exchanger, wherein the catheter is positioned within a fluid filled cavity adjacent to brain tissue, and applying power to the device, thereby modulating the temperature of the brain tissue.

* * * * *